(12) United States Patent
Thoenes

(10) Patent No.: US 6,811,772 B2
(45) Date of Patent: Nov. 2, 2004

(54) COMPOSITION, METHOD, AND APPARATUS TO ATTRACT BEES

(76) Inventor: Steven C. Thoenes, 11358 N. Mandarin La., Tucson, AZ (US) 85737

( * ) Notice: Subject to any disclaimer, the term of this patent is extended or adjusted under 35 U.S.C. 154(b) by 0 days.

(21) Appl. No.: 10/337,187

(22) Filed: Jan. 6, 2003

(65) Prior Publication Data

US 2003/0170283 A1 Sep. 11, 2003

Related U.S. Application Data

(62) Division of application No. 09/568,310, filed on May 8, 2000, now Pat. No. 6,514,511.

(51) Int. Cl.[7] ............................................... A01N 25/10
(52) U.S. Cl. ........................ 424/84; 43/131; 424/405; 424/406; 424/407; 424/411; 449/1; 449/2; 449/7; 514/544; 514/568; 514/718; 514/739
(58) Field of Search ................................ 424/403, 405, 424/407, 409, 411, 84; 449/1, 2, 7; 514/544, 560, 718, 739; 43/131

(56) References Cited

U.S. PATENT DOCUMENTS

| | | | | |
|---|---|---|---|---|
| 1,545,005 A | * | 7/1925 | Meyer et al. | |
| 3,304,646 A | * | 2/1967 | Stagy | 43/131 |
| 4,990,331 A | * | 2/1991 | Slessor et al. | 424/84 |

* cited by examiner

Primary Examiner—Neil S. Levy
(74) Attorney, Agent, or Firm—Dale F. Regelman

(57) ABSTRACT

Applicant's invention includes an improved bee attracting composition. Applicant's invention further includes a bee attracting device formed from his improved bee attracting composition. Applicant's bee attracting device can be further coated with a second bee attracting composition. Applicant's invention further includes a method and apparatus for attracting and immobilizing bees using a substrate coated with an adhesive composition upon which Applicant's bee attracting composition is disposed.

7 Claims, 2 Drawing Sheets

FIG. 4

| COMP. | BUTANOL | BUTYL ACETATE | ISOPENTANOL | ISOPENTYL ACETATE | 2-HEPTANOL | 2-HEPTYL ACETATE | 2-NONANOL | 2-NONANYL ACETATE | BENZYL ACETATE |
|---|---|---|---|---|---|---|---|---|---|
| II | 1 | 1 | 3 | 1 | 3 | 0 | 3 | 3 | 0 |
| JJ | 0 | 5 | 0 | 25 | 0 | 1 | 0 | 1 | 1 |
| KK | 10 | 3 | 10 | 3 | 10 | 3 | 10 | 0 | 3 |
| LL | 1 | 25 | 1 | 25 | 1 | 25 | 1 | 25 | 25 |
| MM | 50 | 10 | 50 | 10 | 50 | 10 | 50 | 10 | 10 |
| NN | 25 | 50 | 5 | 5 | 5 | 5 | 25 | 50 | 50 |
| OO | 5 | 35 | 3 | 50 | 25 | 50 | 5 | 5 | 5 |
| PP | 1 | 1 | 1 | 1 | 1 | 1 | 1 | 1 | 1 |

COMPOSITION, METHOD, AND APPARATUS TO ATTRACT BEES

RELATED APPLICATIONS

This application is a Divisional application of the application having Ser. No. 09/568,310 filed May 8, 2000, now U.S. Pat. No. 6,514,511.

FIELD OF THE INVENTION

The present invention relates to an improved bee attracting composition, an apparatus to attract bees formed from that bee attracting composition, and a method and apparatus using Applicant's improved bee attracting composition to attract and immobilize bees.

BACKGROUND OF THE INVENTION

The immigration of Africanized bees, sometimes referred to as "killer bees," into the United States, and widespread fear of these more defensive bees has increased the public's demand for removal of swarms and feral colonies of bees. At the same time it has made bee removals more problematic. Compared to European bees, Africanized bee colonies swarm more frequently and occur at higher density, so that swarms are more frequently encountered. When swarms or colonies are discovered, there is an increased likelihood that the bees will sting, and a much increased perception that they are dangerous. At the same time, there are fewer beekeepers willing or permitted to perform bee removals. Pest control specialists, and in some areas public agencies, are removing increasing numbers of bee colonies.

Swarms may be removed by hiving them or by spraying them with insecticides, including soap or detergent solutions. A major problem with either technique is that "lost" bees remain at large after most of the bees have been killed or hived. Most of these are bees that were scouting nest sites or foraging away from the swarm cluster when control efforts began. It has been estimated that about 5% of the bees in a swarm participated in scouting one nest site, so in a swarm of 10,000 or more bees, the scouts can comprise several hundred bees. "Lost" bees from a removed swarm remain near the swarm site, but fly around a great deal searching for their queen. These bees can survive for at least several days, and are likely to run short of food, which may make them more likely to sting.

Much has been learned about the behaviors of insects, including bees, in recent years. It is now understood that much of bee behavior arises from use of chemical substances, and mixtures of chemical substances, called "pheromones." A pheromone is a substance secreted by an animal that causes a specific reaction by another individual of the same species. Many bee activities can be explained as the effect of various pheromones.

SUMMARY OF THE INVENTION

Applicants' novel invention includes a bee attracting composition formed by combining aliphatic and aromatic organic compounds which simulate various naturally-occurring honey bee pheromones. Applicant's bee attracting composition can be formed into a solid apparatus which can be used to attract bees.

Applicant's invention further includes an apparatus and method to attract and immobilize bees. This apparatus is formed from a substrate, an adhesive composition, and Applicant's bee attracting composition. The treated substrate can be folded to form a synthetic bee hive. Bees are lured in the interior of the synthetic hive, are drawn to the adhesive component by the bee attracting composition, and become permanently immobilized upon contact with the adhesive.

BRIEF DESCRIPTION OF THE DRAWINGS

The invention will be better understood from a reading of the following detailed description taken in conjunction with the drawings in which like reference designators are used to designate like elements, and in which:

FIG. 4 recites preferred formulations for Applicant's synthetic sting alarm pheromone.

DETAILED DESCRIPTION OF THE PREFERRED EMBODIMENTS

Figure 1:
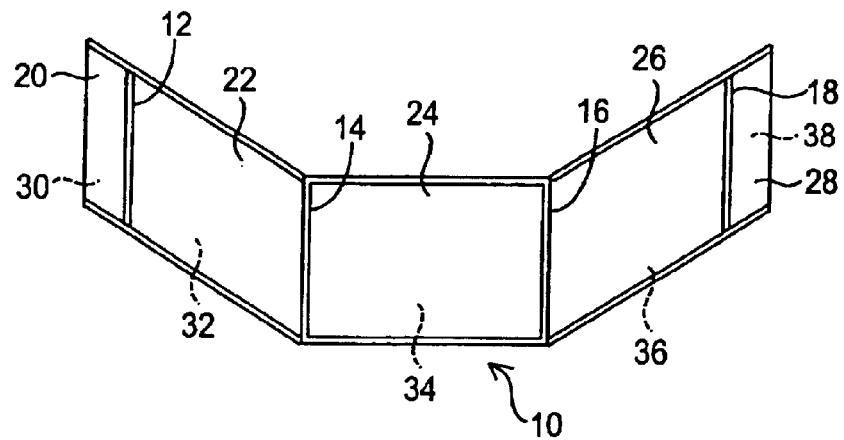
FIG. 1 is a top view of Applicant's substrate.

Applicant has prepared a first bee attracting composition by combining five (5) compounds known to be present in a pheromone composition secreted by queen honey bees, and thought to be formed naturally in the queen bee's mandibular gland. The primary component of Applicant's first composition is 9-keto-2(E)-decenoic acid, which has structure I.

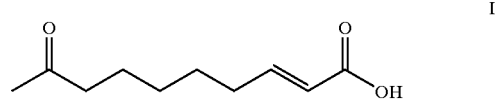

To compound I, Applicant adds two stereoisomers of hydroxydecenoic acid, namely R-(−)-9

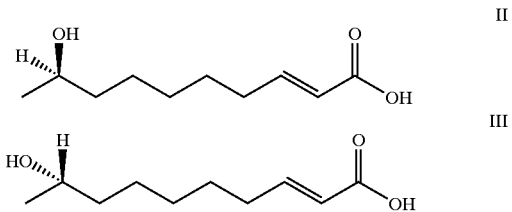

Hydroxy-2(E)-decenoic acid having structure II, and S-(+)-9-Hydroxy-2(E)-decenoic acid having structure III. In general, compounds II and III are present in Applicant's first bee attracting composition in lesser amounts than compound I.

Applicant's first bee attracting composition further includes two aromatic compounds. Methyl p-hydroxybenzoate having structure IV, and 4-Hydroxy-3-methoxyphenylethanol having structure V, are added to aliphatic acids I, II, and III.

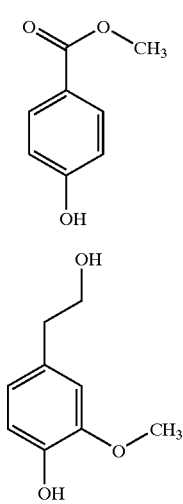

In general, these aromatic compounds are collectively present in Applicant's first bee attracting compositions in lesser amounts than the aggregate amounts of the aliphatic acids discussed above.

Applicant forms his first bee attracting composition by combining between about 25 parts to about 4000 parts compound I, between about 5 parts and about 1000 parts compound II, between about 5 parts and about 200 parts compound III, between about 5 parts and about 100 parts compound IV, and between about 0.1 part to about 10 parts compound V. Table 1 recites the preferred compositions for Applicant's first bee attracting composition.

the attachment device can be joined to the shaped, solid article after molding using conventional techniques, including the use of an adhesive.

Applicant's bee attracting apparatus can be used to induce "lost" bees to preferentially congregate in one specific area. Such a device can be placed away from areas where persons or pets frequent in order to minimize contract between person and/or pets and "lost" bees.

Applicant has found that his first bee attracting composition is effective to attract bees from short ranges, and to keep those bees calm as they congregate around the apparatus containing the composition. Applicant has discovered, however, that a second bee attracting composition more effectively attracts bees from longer ranges. Applicant's second bee attracting composition is a synthetic analog of the naturally-occurring pheromone extracted from worker bees scent gland, sometimes called the Nasanov gland. These Nasanov gland pheromones are sometimes called "releaser" pheromones because, unlike queen bee pheromones, releaser pheromones induce more immediate action from bees.

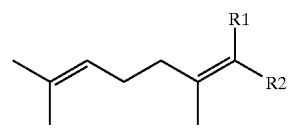

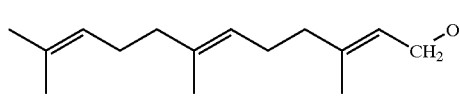

Applicant forms his second bee attracting composition by combining neral, geranial, neral, geranial, nerolic acid,

TABLE 1

| Applicant's Composition | Compound I (Parts) | Compound II (Parts) | Compound III (Parts) | Compound IV (Parts) | Compound V (Parts) |
| --- | --- | --- | --- | --- | --- |
| A | 4000 | 1000 | 200 | 25 | 1 |
| B | 4000 | 500 | 100 | 50 | 1 |
| C | 2000 | 1000 | 200 | 25 | 1 |
| D | 2000 | 500 | 100 | 50 | 1 |
| E | 1000 | 1000 | 200 | 25 | 1 |
| F | 1000 | 500 | 100 | 50 | 1 |
| G | 500 | 500 | 200 | 50 | 1 |
| H | 500 | 250 | 150 | 50 | 1 |
| I | 100 | 100 | 100 | 100 | 1 |
| J | 100 | 100 | 50 | 50 | 1 |
| K | 100 | 50 | 25 | 10 | 1 |
| L | 75 | 50 | 50 | 50 | 1 |
| M | 75 | 50 | 25 | 25 | 1 |
| N | 25 | 5 | 5 | 5 | 1 |

In a separate embodiment, Applicant forms a bee attracting apparatus from his first bee attracting composition. The five constituents discussed above are first dry mixed. The mixture is then heated to a temperature sufficient to completely melt all the individual components. The molten mixture is then made homogeneous through stirring, agitation, or a similar process. The homogeneous melt blend is then cooled to form a solid article. This solid article can be cut into any desired shape or form.

In the alternative, the molten mixture can be placed into a mold. The mold is then allowed to cool, and the shaped, solid article is removed. An attachment device such as a hook, an eyelet, a screw, or a bolt can be joined to the solid article. Such an attachment device can be placed into the mold prior to adding the molten mixture. In the alternative, geranic acid, and E,E-farnesol. Table 2 summarizes the structures of these compounds.

TABLE 2

| COMPOUND | STRUCTURE | R1 | R2 |
| --- | --- | --- | --- |
| Nerol | VI | $CH_2OH$ | H |
| Geraniol | VI | H | $CH_2OH$ |
| Neral | VI | CHO | H |
| Geranial | VI | H | CHO |
| Nerolic Acid | VI | COOH | H |
| Geranic Acid | VI | H | COOH |
| E, E-Farnesol | VII | | |

Applicant's second bee attracting composition is formed by combining between about 0.1 part and about 500 parts neral, between about 0.1 part and about 500 parts geranial, between about 0 parts and about 500 parts nerol, between about 0.1 part and about 500 parts geraniol, between about 0.1 part and about 500 parts nerolic acid, between about 0.1 part and about 500 parts geranic acid, and between about 0 parts and about 500 parts E,E-farnesol. Table 3 sets forth preferred formulations for Applicant's second bee attracting composition.

TABLE 3

| Embodiment | Neral (Parts) | Geranial (Parts) | Nerol (Parts) | Geraniol (Parts) | Nerolic Acid (Parts) | Geranic Acid (Parts) | Farnesol |
|---|---|---|---|---|---|---|---|
| O | 1 | 1 | 1 | 1 | 1 | 1 | 1 |
| P | 1 | 3 | 1 | 1 | 3 | 1 | 0 |
| Q | 1 | 3 | 1 | 1 | 3 | 1 | 3 |
| R | 1 | 3 | 3 | 1 | 3 | 1 | 0 |
| S | 1 | 5 | 0 | 1 | 3 | 1 | 3 |
| T | 3 | 3 | 1 | 3 | 3 | 1 | 0 |
| U | 5 | 1 | 1 | 5 | 1 | 1 | 5 |
| V | 5 | 5 | 0 | 5 | 5 | 1 | 0 |
| W | 5 | 1 | 5 | 5 | 1 | 5 | 5 |
| X | 1 | 5 | 0 | 1 | 5 | 5 | 0 |

A second bee attracting apparatus is formed using Applicant's first bee attracting composition in combination with Applicant's second bee attracting composition. The solid apparatus formed from melt blending and molding Applicant's first bee attracting composition is coated with Applicant's second bee attracting composition to form a bee attracting device having enhanced long range bee attracting capabilities in combination with enhanced short range effects.

Another class of "releaser" bee pheromones, sometimes referred to as a "sting alarm pheromone," is thought to elicit mass action in the form of an attack on a potential predator. Applicant has discovered that a synthetic analog of this sting alarm pheromone effectively attracts bees. Applicant's third bee attracting composition comprises a synthetic sting alarm pheromone which is formed by combining two or more of the following compounds in the following amounts: up to about 50 parts butanol, up to about 50 parts butyl acetate, up to about 50 parts isopentanol, up to about 50 parts isopentyl acetate, up to about 50 parts 2-heptanol, up to about 50 parts 2-heptyl acetate, up to about 50 parts 2-nonanol, up to about 50 parts 1-non-2-enyl acetate, and up to about 50 parts benzyl acetate. FIG. 4 recites preferred embodiments of Applicant's third bee attracting composition.

Applicant has discovered that the presence of additional compounds thought to be formed in bee scent glands further enhances the effectiveness of his bee attracting composition. These additional scent compounds include hexadecan-1-yl acetate, pentadecane, neryl acetate, geranyl acetate, farnesyl acetate. Applicant's fourth bee attracting composition is formed by combining between 0 and about 50 parts hexadecan-1-yl acetate, between 0 and about 50 parts pentadecane, between 0 and about 50 parts neryl acetate, between 0 parts and about 50 parts geranyl acetate, and between 0 parts and about 50 parts farnesyl acetate. Table 4 recites preferred compositions for Applicant's fourth bee attracting composition.

TABLE 4

| Composition | Hexadecan-1-yl acetate (parts) | Penta-decane (parts) | Neryl acetate (parts) | Geranyl acetate (parts) | Farnesyl acetate (pails) |
|---|---|---|---|---|---|
| Y | 10 | 10 | 10 | 10 | 10 |
| Z | 25 | 0 | 25 | 0 | 0 |
| AA | 0 | 25 | 0 | 25 | 0 |

TABLE 4-continued

| Composition | Hexadecan-1-yl acetate (parts) | Penta-decane (parts) | Neryl acetate (parts) | Geranyl acetate (parts) | Farnesyl acetate (pails) |
|---|---|---|---|---|---|
| BB | 25 | 0 | 0 | 0 | 25 |
| CC | 25 | 25 | 0 | 0 | 0 |
| DD | 0 | 25 | 25 | 0 | 0 |
| EE | 0 | 25 | 0 | 25 | 0 |
| FF | 0 | 25 | 0 | 0 | 25 |
| GG | 0 | 0 | 25 | 0 | 25 |
| HH | 0 | 0 | 0 | 25 | 25 |

Applicant's fifth bee attracting composition is formed by combining Applicant's first bee attracting composition with Applicant's second bee attracting composition. In this embodiment, Applicant's first composition is present between about 1 to about 1000 parts per 100 parts of Applicant's second composition.

Applicant's sixth bee attracting composition is formed by combining his first bee attracting composition with his third bee attracting composition wherein Applicant's first composition is present between about 1 to about 1000 parts per 100 parts of Applicant's third composition. Applicant's seventh bee attracting composition is formed by combining his first bee attracting composition with his fourth bee attracting composition wherein the fourth composition is present between about 1 to about 1000 parts per 100 parts of first composition.

Applicant's eighth bee attracting composition is formed by combining Applicant's first, second, and third bee attracting compositions, such that the second composition is present between about 1 to about 1000 parts per 100 parts of first composition, and the third composition is present between about 1 to about 1000 parts per 100 parts of first composition. In this embodiment, the second composition and the third composition may be present in equal or different amounts.

Applicant's ninth bee attracting composition is formed by combining Applicant's first, second, third, and fourth bee attracting compositions, such that the second composition is present between about 1 to about 1000 parts per 100 parts of first composition, the third composition is present between about 1 to about 1000 parts per 100 parts of first composition, and the fourth composition is present between about 1 to about 1000 parts per 100 parts of first composition. In this embodiment, Applicant's second, third, and fourth bee attracting compositions may be present in equal or different amounts.

Applicant's tenth bee attracting composition is formed by combining Applicant's second and third bee attracting compositions, such that the third composition is present between about 1 to about 1000 parts per 100 parts of second composition.

Applicant's eleventh bee attracting composition is formed by combining Applicant's second and fourth bee attracting compositions, such that the fourth composition is present between about 1 to about 1000 parts per 100 parts of second composition.

Applicant's twelfth bee attracting composition is formed by combining Applicant's third and fourth bee attracting compositions, such that the fourth composition is present between about 1 to about 1000 parts per 100 parts of third composition.

Applicant's thirteenth bee attracting composition is formed by combining Applicant's second, third, and fourth bee attracting compositions, such that the third composition is present between about 1 to about 1000 parts per 100 parts of second composition, and the fourth composition is present between about 1 to about 1000 parts per 100 parts of second composition. In this embodiment, the third composition and the fourth composition may be present in equal or different amounts.

In a separate embodiment, Applicant's invention includes a method and apparatus to attract and to immobilize "lost" bees. In this embodiment, a pressure sensitive adhesive is disposed on at least one side of a substrate. The substrate can be formed from paper, wood, metal, plastic, and combinations thereof. The substrate can be formed from either rigid or flexible material.

In one embodiment, the substrate includes a plurality of creases which define fold points. Referring to FIG. 1, the top surface of substrate 10 is shown including fold points 12, 14, 16, and 18. These fold points define top-surface areas 20, 22, 24, 26, and 28. The bottom surface of substrate 10 includes areas 30, 32, 34, 36, and 38. FIG. 1 shows areas 22 and 26 bent slightly upward from area 24.

Figure 2:
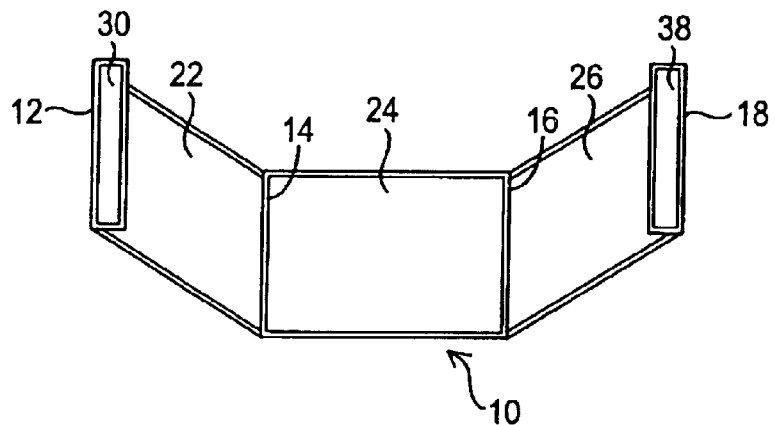
FIG. 2 is a top view of Applicant's partially folded substrate.
Figure 3:
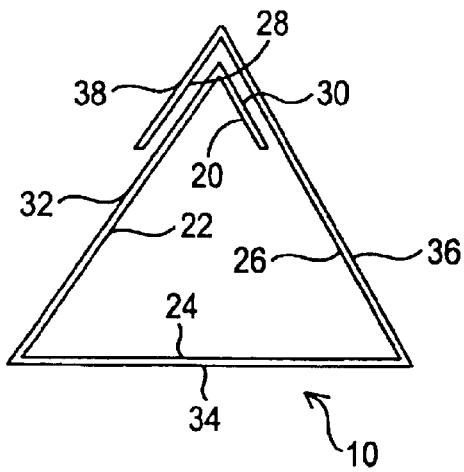
FIG. 3 is a side view of one embodiment of Applicant's invention wherein the substrate is folded into a triangular configuration.

Referring to FIG. 2, end areas 20 and 30 have been folded inwardly to expose bottom surface areas 30 and 38. Referring to FIG. 3, substrate 10 has been folded to form a triangular apparatus having outside surfaces 32, 34, and 36, wherein end area 38 overlaps surface 32.

Applicant's substrate can be folded to form an apparatus having the shape of a square, pentagon, hexagon, heptagon, octagon, nonagon, decagon, or any other multi-sided shape wherein the individual sides are of either equal or differing lengths.

The pressure sensitive adhesive can comprise naturally-occurring materials, synthetic adhesives, or mixtures of both. For example, certain pitches or plant resins can be used as the adhesive. In one embodiment, pitch from pine trees is used as the adhesive. In another embodiment, resins from genus Hymenaea is used. These leguminous, flowering trees pump out astonishing quantities of sticky resins.

Natural rubber-based pressure sensitive adhesives are preferred. Synthetic adhesives may also be used. For example, the adhesive component of this embodiment can include polyacrylate-based compositions wherein the ester group comprises an alkyl group having between about 4 and 10 carbons, natural rubbers grafted with such polyacrylates, triblock adhesive compositions formed from polystyrene/polyisoprene/polystyrene, and mixtures of these synthetic adhesive compositions.

The adhesive component is applied to the substrate using conventional methods including spraying, rolling, or calendaring. The adhesive is applied at a rate of between 1 gram to about 1000 grams for each square meter of surface area of the substrate.

One of Applicant's bee attracting compositions is then applied to the surface of the adhesive composition. Any one or combination of Applicant's afore-described thirteen bee attracting compositions may be used. In one embodiment, between about 1 microgram to about 1 gram of bee attracting composition is applied to each square meter surface area of adhesive-covered substrate. In a separate embodiment, between about 10 micrograms to about 10 milligrams of bee attracting composition is applied to each square meter of adhesive-covered substrate. In another embodiment, between about 100 micrograms and about 1 milligram of bee attracting composition is applied to each square meter of adhesive-coated substrate.

In another embodiment, the adhesive component and the bee attracting composition are first mixed together, and that mixture is then applied to at least one side of Applicant's substrate, such that between about 1 microgram to about 1 gram of bee attracting composition is applied to each square meter surface area of adhesive-covered substrate. In a separate embodiment, the adhesive component/bee attracting component mixture is applied such that between about 10 micrograms to about 10 milligrams of bee attracting composition is applied to each square meter of adhesive-covered substrate. In another embodiment, the adhesive/bee attracting composition mixture is applied such that between about 100 micrograms and about 1 milligram of bee attracting composition is applied to each square meter of adhesive-coated substrate.

Regardless of whether the adhesive component and bee attracting component are separately or jointly applied to the substrate, Applicant's bee attracting composition can be disposed on one or both surfaces of Applicant's substrate. If the bee attracting component is applied to only one surface, the interior surfaces of the resulting folded apparatus are preferably coated with adhesive and bee attracting component. Referring again to FIG. 3, interior surfaces 22, 24, and 26 are preferably coated with Applicant's adhesive component and Applicant's bee attracting composition.

When folded into an apparatus having a contiguous outer surface, Applicant's substrate comprises an enclosed object with openings at both ends. In this embodiment, Applicant's invention comprises a synthetic bee hive. Lost bees are attracted from long distances by Applicant's bee attracting composition. When approaching the synthetic hive, the bees are lured into the interior. Applicant's novel bee attracting composition entices the bees to come into physical contact with the adhesive component disposed on the inner surfaces of the synthetic hive. Upon contact with those adhesive-coated walls, the bees are instantly and permanently immobilized. The synthetic hive carrying the immobilized bees is easily disposed of, thereby, allowing untrained persons to effectively and safely handle "lost" bees.

An additional feature of Applicant's invention arises from the placement of adhesive on the interior surfaces of the synthetic hive. Referring again to FIG. 3, because surface area 28 is coated with Applicant's adhesive component, area 28 will adhere to outer surface 32 without the need for any additional attachment devices. Thus, Applicant's substrate can be folded to form a contiguous apparatus having any number of sides, and that contiguous apparatus will readily maintain its folded shape.

Optionally, Applicant's bee attracting composition can be applied to both surfaces of Applicant's substrate. This embodiment is preferred when the substrate is used in a planar or substantially planar shape, i.e. in an unfolded configuration. In this embodiment, the adhesive component and the bee attracting component may be sequentially applied to the substrate, or may be mixed and then jointly applied to the substrate.

I claim:

1. An apparatus to attract and immobilize bees, comprising:
   a substrate having a first side and a second side, and a first end and a second end;
   an adhesive composition disposed on at least one of said sides of said substrate; and
   a bee attracting composition disposed on said adhesive composition, wherein said bee attracting composition comprises:
   4-hydroxy-3-methoxyphenylethanol;
   methyl 4-hydroxybenzoate;
   9-keto-2(E)-decenoic acid;
   R-(−)-9-hydroxy-2(E)-decenoic acid;
   S-(+)-9-hydroxy-2(E)-decenoic acid;
   geranial;
   neral;
   geranial;
   nerolic acid;
   geranic acid; and
   farnesol;
   wherein:
   said 4-hydroxy-3-methoxyphenylethanol is present in an amount between about 0.1 parts and about 10 parts;
   said methyl 4-hydroxybenzoate is present in an amount between about 5 parts and about 200 parts;
   said S-(+)-9-hydroxy-2(E)-decenoic acid is present in an amount between about 5 parts and about 200 parts;
   said R-(−)-9-hydroxy-2(E)-decenoic acid is present in an amount between about 5 parts and about 1000 parts;
   said 9-keto-2(E)-decenoic acid is present in an amount between about 25 parts and about 4000 parts;
   said geranial is present in an amount between about 0.1 parts and about 500 parts;
   said neral is present in an amount between about 0.1 parts and about 500 parts;
   said geranial is present in an amount between about 0.1 parts and about 500 parts;
   said nerolic acid is present in an amount between about 0.1 parts and about 500 parts;
   said geranic acid is present in an amount between about 0.1 parts and about 500 parts; and
   said farnesol is present in an amount between about 1 part and about 5 parts.

2. The apparatus of claim 1, wherein said substrate is formed from a rigid material selected from the group consisting of wood, metal, plastic, and mixtures thereof.

3. The apparatus of claim 1, wherein said substrate is formed from a flexible material selected from the group consisting of wood, metal, plastic, and mixtures thereof.

4. The apparatus of claim 1, wherein said adhesive composition is selected from the group consisting of naturally occurring pitches, resins, and mixtures thereof.

5. The apparatus of claim 1, wherein said adhesive composition is a pressure sensitive adhesive.

6. The apparatus of claim 1, wherein said first end of said substrate is attached to said second end of said substrate.

7. The apparatus of claim 1, wherein said adhesive composition is disposed on both of said sides of said substrate.

* * * * *